United States Patent [19]
Andrese

[11] Patent Number: 5,904,649
[45] Date of Patent: *May 18, 1999

[54] ORGAN RETRACTORS

[76] Inventor: Craig A. Andrese, 128 Stirrup La., Burr Ridge, Ill. 60521

[21] Appl. No.: 09/062,596

[22] Filed: Apr. 17, 1998

Related U.S. Application Data

[60] Provisional application No. 60/080,549, Apr. 3, 1998.

[51] Int. Cl.[6] .................................................... A61B 17/00
[52] U.S. Cl. ........................... 600/204; 600/211; 600/216
[58] Field of Search .................................... 600/201, 204, 600/206, 210, 211, 214, 215, 216, 219, 224

[56] References Cited

U.S. PATENT DOCUMENTS

| | | |
|---|---|---|
| 5,176,128 | 1/1993 | Andrese . |
| 5,235,966 | 8/1993 | Jamner ................................ 600/216 X |
| 5,284,128 | 2/1994 | Hart .................................... 600/215 X |
| 5,662,676 | 9/1997 | Koninckx ............................ 600/210 X |

*Primary Examiner*—Jeffrey A. Smith
*Attorney, Agent, or Firm*—Patnaude & Videbeck

[57] ABSTRACT

An improved organ retractor includes an elongate handle and a rigid stem extending from one end of the elongate handle. A hollow sleeve is positioned around the stem and is axially slidable along the stem from a retracted position partly inside of said handle to an extended position. The sleeve is bifurcated or divided axially in half adjacent a distal end thereof to define two opposed elongate resilient fingers. The distal ends of each of the fingers are movable from a closed position wherein those distal ends are substantially adjacent each other surrounding the rigid stem to an open position wherein the distal ends are spaced from each other. A connector arm is positioned between each of the fingers and the rigid stem. The connector arms move the fingers to an open position when the stem is in one of the retracted and extended positions and move the fingers to a closed position when the stem is in the other of the retracted and extended positions. In a second embodiment of the invention, the opposed resilient fingers include a plurality of digits serially pivotally mounted to each other along the length of each finger.

8 Claims, 3 Drawing Sheets

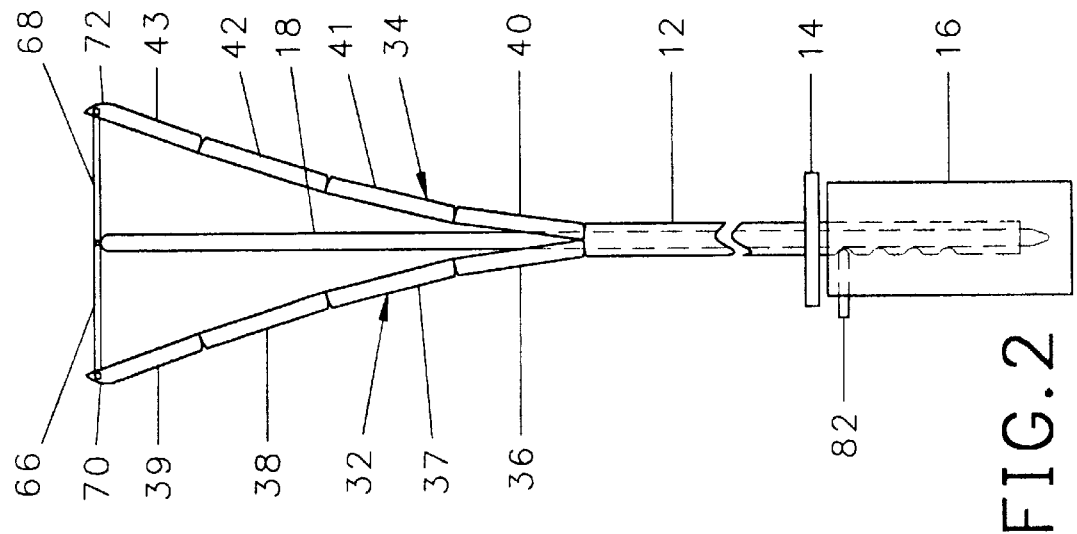
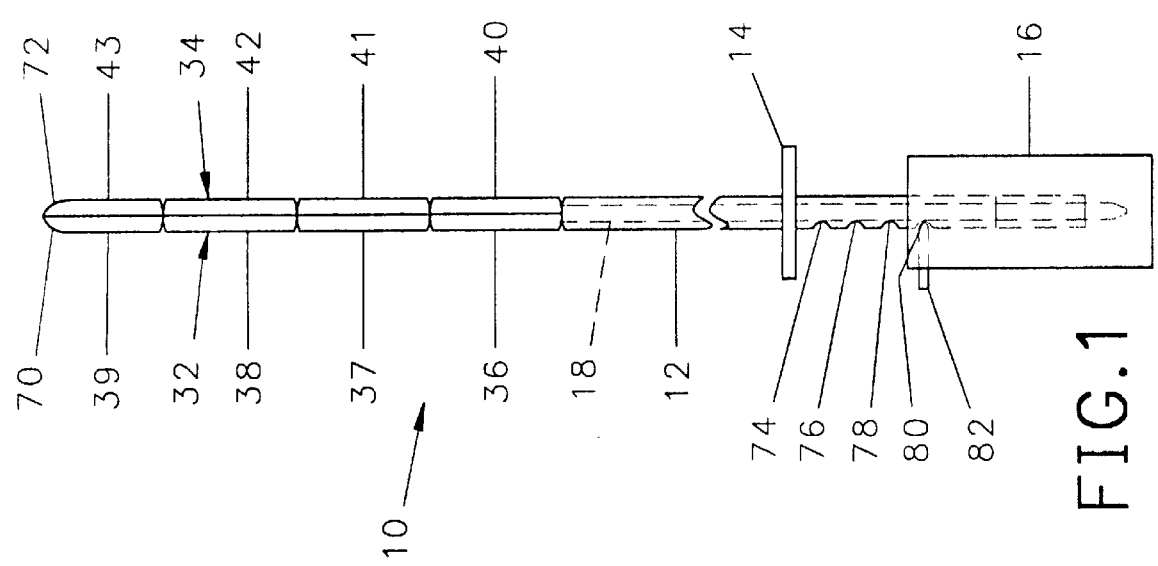

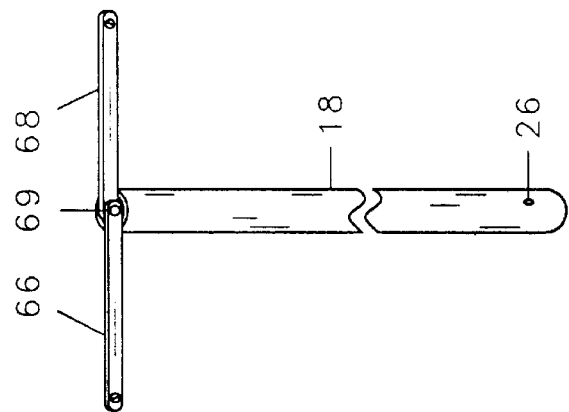
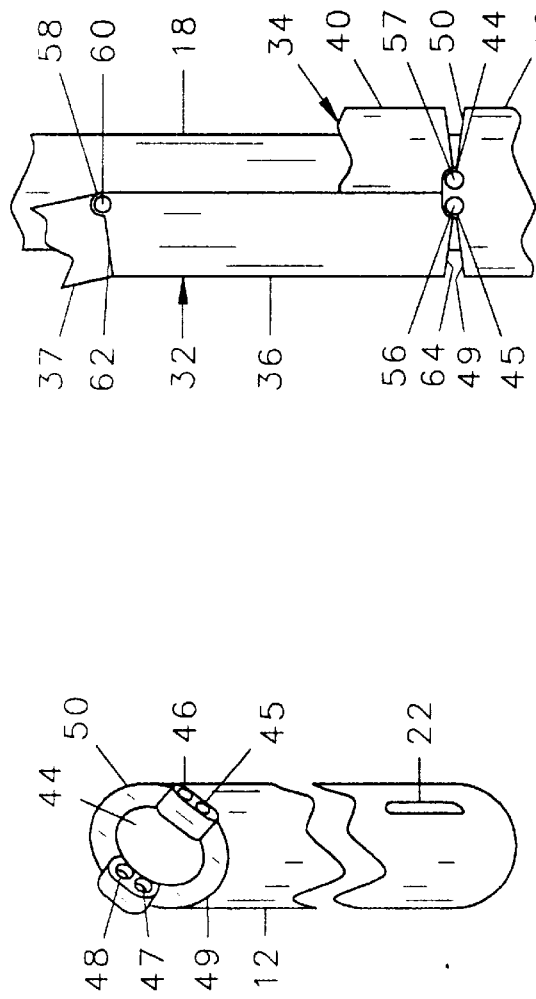
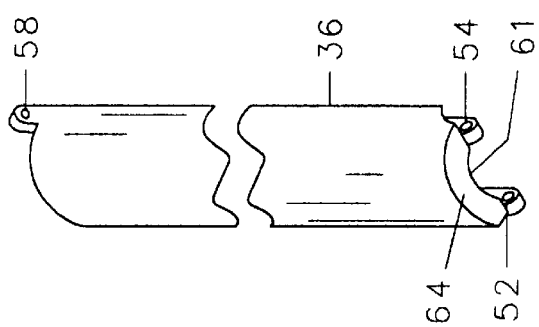

ORGAN RETRACTORS

This application claims the benefit of U.S. Provisional Application No. 60/080,549 filed Apr. 3, 1998.

The present invention relates to surgical instruments and in particular to improved instruments employed to retain the internal organs of the body in a desired orientation during various surgical procedures, including laproscopic surgery.

BACKGROUND OF THE INVENTION

Endoscopic surgery procedure can be performed by inserting instruments through a small incisions through a body wall. During the surgery, pressurized gas can be introduced into the body cavity to move the skin and muscles away from the organ or organs requiring surgery. Internal organs can move under the force of gravity, however, and in some cases an instrument may be needed to move and retain the organs in a desired orientation during the procedure.

In my U.S. Pat. No. 5,176,128, I disclosed an organ retractor having a plurality of fingers for insertion into a body cavity to assist in moving organs and retaining them in a desired orientation during laproscopic surgery. The organ retractor disclosed therein, however, has a plurality of fingers made of spring steel or the like which are biased to separate their distal ends from one another unless they are retained by a plurality of strings movable through a central shaft. To control the operation of my previous organ retractor one must rely upon the spring bias of the various fingers for maintaining the spacing of the distal finger ends.

It would be desirable to provide an organ retractor with expansible members whose movement is controlled by the surgeon without the use of pre-biased members.

SUMMARY OF THE INVENTION

In accordance with the invention, the organ retractor has a pair of substantially parallel pliable fingers, each of the pliable fingers having a distal end. A rigid stem having an axis substantially parallel with the length of the fingers is positioned between the fingers and is fixed in position. In one embodiment of the invention, the fingers are jointed to permit the distal ends thereof to be movable from a closed position wherein the distal ends thereof are substantially adjacent to each other with the fingers aligned along the stem, to an open position wherein the distal ends of the fingers are spaced from each other. The fingers are slidable along the stem. A connector arm extends between each of the fingers and the rigid stem. In this embodiment, the arms are aligned perpendicularly to the stem when the fingers are in the extended condition and the arms are aligned parallel to the stem when the fingers are in the retracted position. Axial movement of the fingers into the extended position will, therefore, separate the distal ends of the fingers while movement of the fingers to the retracted condition will draw the distal ends of the fingers against the stem, that is into the closed position. In another embodiment of the invention, the fingers are unitary structures having a plurality of spaced bendable narrower portions therealong facilitating elastic bending of the fingers from a closed position to an open position similarly to the first embodiment. To employ the organ retractor during the procedure the axially moveable fingers are extended to orient the distal ends of the thereof in a closed position such that the retractor can be moved through an introducer and into the body cavity of a patient. Once within the cavity the fingers may be axially moved to change the orientation of the connector arms and force the distal ends of the fingers away from one another and into an open position.

BRIEF DESCRIPTION OF THE DRAWINGS

A better understanding of the present invention can be had from a reading of the following detailed description taken in conjunction with the drawings wherein:

FIG. 1 is a side elevational view of a first embodiment an organ retractor constructed in accordance with the present invention with its fingers in the closed position and with portions of its interior shown in phantom line;

FIG. 2 is a front elevational view of the organ retractor shown in FIG. 1 with its fingers in open position and with portions of its interior shown in phantom line;

FIG. 3 is a fragmentary enlarged isometric view of the central body of the organ retractor shown in FIG. 1;

FIG. 4 is an enlarged fragmentary view of one of the jointed sections of a retractor finger;

FIG. 5 is an enlarged fragmentary front view of the retractor shown in FIG. 1 showing the connection of the central body to the fingers, including one section of one finger;

FIG. 6 is an enlarged fragmentary view of the stem and the arms attached thereto;

DETAILED DESCRIPTION OF THE PREFERRED EMBODIMENTS

Figure 8:
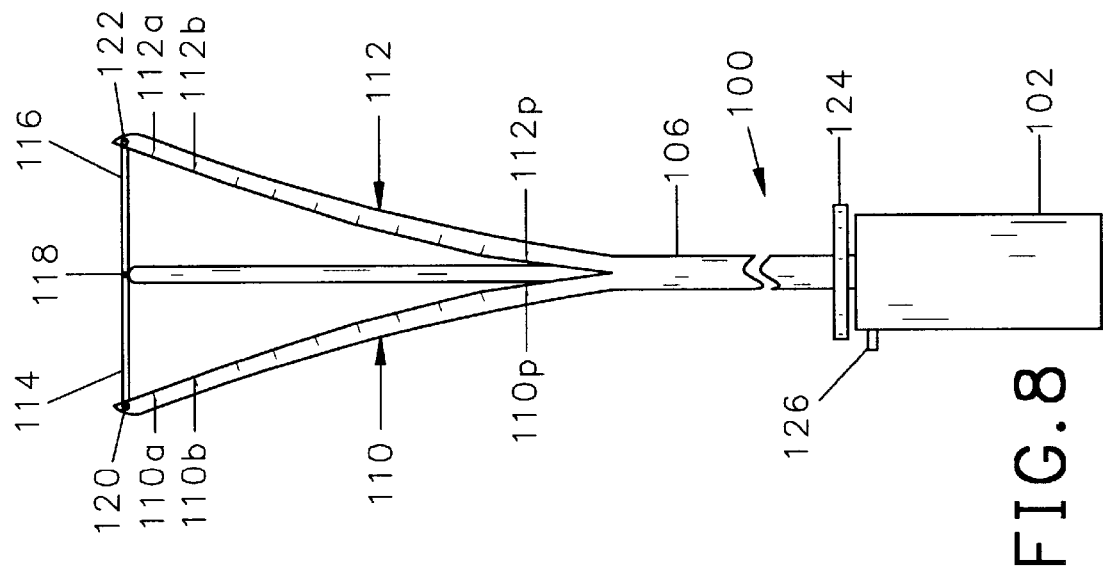
FIG. 8 is a front elevational view of the embodiment shown in FIG. 7 in fully open position.

Referring to FIGS. 1, 2, 3, and 6 a first embodiment of an organ retractor 10 has a generally tubular sleeve 12 having a centrally located radial flange 14. Tubular sleeve 12 is axially slidable along a central handle 16. Extending axially through the center of the tubular sleeve 12 is an elongate stem 18 fixed on the bottom of central body 16. The sleeve slides in and out of the handle 16 with locking pin 82 movably positioned within the handle and being interfaced between the sleeve 12 and the handle 16 at indentations 74–80. The pin's purpose is to limit any in or out movement of the sleeve 12 over the stem 18, thereby maintaining stability of the open distal ends 70–72 of the fingers. The flange 14 is connected to the sleeve 12 in a rigid fashion enabling the surgeon to move the sleeve 12 axially into and out of the handle 16.

Referring to FIGS. 3, 4 and 5, at the forward end of the tubular sleeve 12 are two pairs of pivot eyes 45, 46, 47, 48. As best shown in FIG. 5, the sleeve 12 has inclined forward surfaces 49, 50 which slope gently away from the eyes 45–48. Pivotally connected to the forward end of the sleeve 12 through the eyes 45–48 are jointed fingers, generally indicated at 32, 34, where finger 32 has joined sections 36, 37, 38 and 39 and finger 34 has joined sections 40, 41, 42 and 43. The central opening 44 of the sleeve 12 has a diameter which is a little larger than the diameter of the stem 18 to permit axial movement of the sleeve relative to the stem.

Referring to FIGS. 4 and 5, the joined fingers 32, 34 are mirror images of one another such that finger 32 is representative of both, and the central sections thereof 36, 37, 38, 40, 41, 42 are all identical such that section 36 is representative of all. As can be seen, section 36 has a pair of spaced eyes 52, 54 at the rearward end thereof which are spaced to fit between eyes 45, 47 of the sleeve 12 and be retained therein by pins 56, 57. Similarly, the forward end of section 36 has a pair of spaced eyes, one of which 58 is visible.

Through the eyes 58 are pins 60 for attaching the forward end thereof to the next jointed section 37. In similar fashion, all of the sections 36–43 are pivotally attached to form the parallel jointed fingers 32, 34, respectively.

The inner surface 61 of the sections 36 are cylindrical with an inner diameter a little larger than the outer diameter of the stem 18, so that when the sections are linearly assembled around the stem 18, as shown in FIG. 1, are axially movable the sections 36–43 of the fingers 32, 34, along the stem 18.

Referring to FIG. 5, the forward surface 62 and rearward surface 64 of each section 36 bears a gentle ramp such that the sections 36, 43 are movable from the first position in which adjacent sections are linearly aligned with respect to one another to a second position in which adjacent sections are angled with respect to one another. In FIG. 5, sections 36 and 40 are depicted as being linearly aligned with respect to the sleeve 12 whereas sections 36 and 37 are depicted in angled alignment with respect to each other. FIG. 1 depicts the fingers 32, 34 in the first closed position with the sections thereof in linear alignment with one another whereas FIG. 2 depicts the fingers 32, 34 in the second open position in which the various sections are in angled relationship to one another.

As best shown in FIGS. 2 and 6, the distal end of the stem 18 is pivotally connected to one end of each of a pair of arms 66, 68 by a pin 69. The opposite end of arm 66 is pivotally connected to the distal end 70 of section 39 of joined finger 32 and the opposite end of arm 68 is pivotally connected to the distal end 72 of joined finger 34. Downward movement of the sleeve 12 causes the flange 14 as shown in FIG. 2 and the fingers 70–72 to move relative to the distal end of the stem 18, such that the arms 66, 68 are aligned in end to end horizontal relationship, as shown. The distal ends 70, 72 of the fingers 32, 34 are thereby rigidly retained in spaced relationship to one another. Conversely, the upward movement of the sleeve 12 and flange 14 will cause the arms 66, 68 to be oriented parallel to one another, and the joined fingers 32, 34 positioned parallel to one another as shown in FIG. 1.

Figure 7:
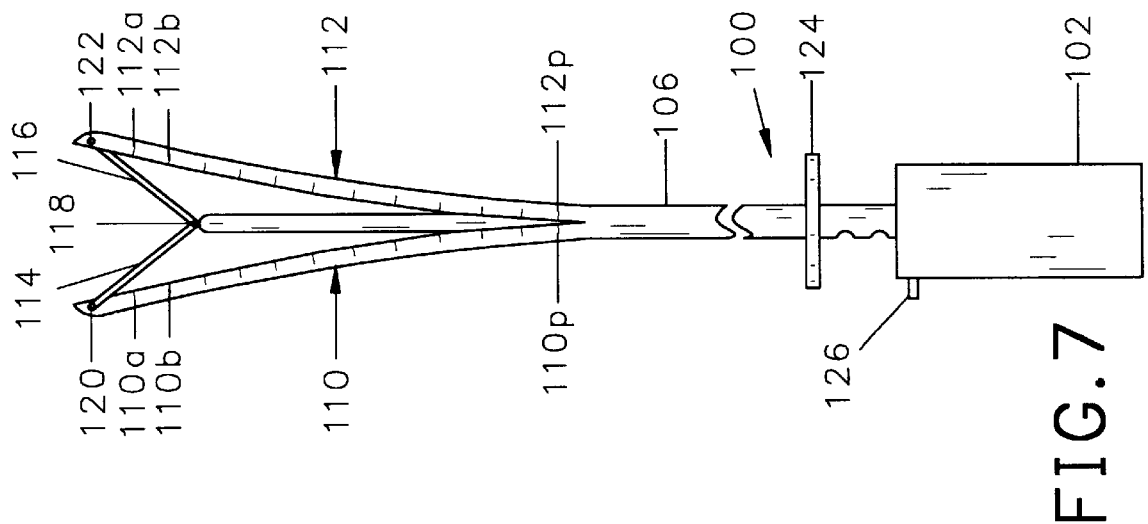
FIG. 7 is a front elevational view of a second embodiment of the present invention in partially open position.

Referring to FIGS. 7 and 8, a second embodiment of the organ retractor of the present invention, generally indicated at 100, includes a hollow handle 102 having a tubular sleeve fit in the hollow area therein for reciprocating motion with respect to the handle. As in the first embodiment, a central stem 108 is positioned rigidly with respect to the handle 102, such that the sleeve 106 is reciprocatively slidable along the stem 108. Part way up the tubular sleeve 106, as it extends from the hollow handle 102, the sleeve is bifurcated into elongate arcuately cross-sectioned finger portions 110, 112, respectively. The bifurcated fingers 110, 112, if made of elastic material, may have an unvarying cross-section along its length from the sleeve 102 to the distal end of each arm. If the arms are made of a relatively rigid tubular material, such as stainless steel or the like, a plurality of grooves 110a–110p, 112a–112p, respectively, providing a plurality of thinner bridging portions at the central solid portion of each of the bifurcated, arcuate cross-section arms. This multisegmented structure provides a solid mechanism which is more flexible than a solid arm would be. The smaller bridging portions on each of the arcuate fingers 110, 112 would act in a similar fashion to each of the pivot pins disclosed in the first embodiment. Also as in the first embodiment 10, the second embodiment 100 includes a pair of arms 114, 116, which extend pivotally between the distal end of stem 108 and the distal ends of each of the bifurcated fingers 110, 112. Arms 114, 116 are attached to the distal end of the stem 108 by pivot pin 118 and to each of the bifurcated cross section arms by pivot pins 120, 122, respectively. In other respects, the handle 102, and the sleeve 106 of the organ retractor 100, operate similarly to organ retractor 10, including the operation of the radial flange 124 and the locking pin 126.

As shown most clearly in FIGS. 7 and 8, the second embodiment of the organ retractor 100 is operated such that moving the tubular sleeve 106 up and down with respect to the handle 102 allows the distal ends of the bifurcated, arcuate cross-sectional fingers 110, 112 to be moved outwardly by the relative swinging movement of the arms 114 and 116 pivotally around the distal end of the stem 108. As shown in open position in FIG. 8 and in semi-closed position in FIG. 7.

There is, therefore, disclosed an organ retractor which can be inserted into a body cavity and which may be manually adjusted by the physician to rigidly retain the distal ends of the instrument in a desired spaced relationship to one another to provide an expanding grid-like structure adapted to move body organs allowing a surgeon access to other organs facilitating the operation of surgical procedures.

While two embodiments of the present invention have been shown and described, it will be apparent to those skilled in the art that many changes and modifications may be made without departing from the true spirit and scope of the present invention. It is the intent of the appended claims to cover all such changes and modifications which fall within the true spirit and scope of the invention.

What is claimed:

1. An organ retractor comprising in combination:
    an elongate handle,
    a rigid stem extending from one end of said elongate handle,
    a hollow sleeve positioned around said stem and axially slidable therealong from a retracted position to an extended position, said sleeve being bifurcated adjacent a distal end thereof defining two opposed resilient fingers, each of said fingers including more than two serially oriented digits,
    said distal ends of each of said fingers being movable from a closed position wherein said distal ends are substantially adjacent each other surrounding said rigid stem to an open position wherein said distal ends are spaced from each other, and each digit subjacent said distal end being closer to said rigid stem than the digit suprajacent thereto when said fingers are in an open position,
    a connector arm positioned between each of said fingers and said rigid stem, said connector arms moving said fingers to said open position when said stem is in one of said retracted position and said extended position, and moving said fingers to said closed position when said stem is in the other of said retracted position and said extended position.

2. The organ retractor as defined in claim 1 wherein said serially oriented digits are pivotally mounted to one another.

3. The organ retractor as defined in claim 1 wherein each of said connector arms is a pivotal link pivotally mounted at one end thereof to a first interior pivotal mounting on one of said opposed resilient fingers and pivotally mounted at an opposite end thereof to a second pivotal mounting adjacent a distal end of said stem.

4. An organ retractor comprising in combination,
    a elongate body,
    a rigid stem extending from one end of said body a plurality of substantially parallel jointed fingers axially slidable along said stem from a retracted position to an extended position, each of said fingers having a distal end, said distal ends of said fingers movable from a closed condition wherein said distal ends are substantially adjacent each other to an open condition wherein said distal ends are spaced from each other, a connector arm between each of said fingers and said rigid stem said connector arms for moving said fingers to said open condition when said stem is in one of said retracted position and said extended position and moving said fingers to said closed condition when said stem is in the other of said retracted position and said extended position, and locking means positioned on said body and acting on said stem for selectively retaining and releasing said distal end in a plurality of discrete spacing positions from one another.

5. An organ retractor in accordance with claim 4 and further comprising control means movable with respect to said body, and connector means connecting said control means to said fingers whereby said fingers are axially movable by movement of said control means.

6. An organ retractor in accordance with claim 4 wherein each of said fingers thereof further comprises, a plurality of digits having opposed ends, pivot connector means on at least one of said ends of said digits, and an angled surface at said one end of said digit.

7. An organ retractor in accordance with claim 4 and further comprising control means movable relative to said body, connector means connecting said control means to said fingers whereby said fingers are axially movable by movement of said control means, locking means on said body and said control means for selectively releasably locking said fingers with respect to said body, each of said fingers having a plurality of digits, each of said digits have a pivot connection means on at least one end thereof, and each of said digits having an angled surface on at least one end thereof.

8. An organ retractor comprising in combination:

an elongate handle, a rigid stem extending from one end of said elongate handle, a hollow sleeve positioned around said stem and axially slidable therealong from a retracted position to an extended position, said sleeve being bifurcated adjacent a distal end thereof defining two opposed resilient fingers, said distal ends of each of said fingers being movable from a closed position wherein said distal ends are substantially adjacent each other surrounding said rigid stem to an open position wherein said distal ends are spaced from each other, each of said resilient fingers being divided into more than two segments serially connected along their length, each said serial connection including a narrowed bendable bridging portion between each said segment and bevelled surfaces from said bridging portion to an opposing side of each of said segments for providing space to allowing each of said segments to bend relative to an adjacent segment thereof, each segment subjacent said distal end being closer to said rigid stem than the segment suprajacent thereto when said fingers are in an open position, a connector arm positioned between each of said fingers and said rigid stem, said connector arms moving said fingers to said open position when said stem is in one of said retracted position and said extended position, and moving said fingers to said closed position when said stem is in the other of said retracted position and said extended position.

* * * * *